United States Patent [19]

Hoffman et al.

[11] Patent Number: 4,693,237

[45] Date of Patent: Sep. 15, 1987

[54] RADIOPAQUE CODED RING MARKERS FOR USE IN IDENTIFYING SURGICAL GRAFTS

[76] Inventors: Richard B. Hoffman, 73 Portugese Bend Rd.; Jonathan B. Po, 68 Portugese Bend Rd., both of Rolling Hills, Calif. 90274

[21] Appl. No.: 820,307

[22] Filed: Jan. 21, 1986

[51] Int. Cl.⁴ .............................................. A61B 19/00
[52] U.S. Cl. ..................................................... 128/1 R
[58] Field of Search ................................ 128/1 R, 638

[56] References Cited

U.S. PATENT DOCUMENTS

| | | | |
|---|---|---|---|
| 3,625,212 | 12/1971 | Rosenberg et al. | 604/6 X |
| 4,041,931 | 8/1977 | Elliot et al. | 128/1 R |
| 4,150,673 | 4/1979 | Watt | 604/110 X |
| 4,202,349 | 5/1980 | Jones | 128/1 R |

*Primary Examiner*—Stephen C. Pellegrino
*Attorney, Agent, or Firm*—Edward A. Sokolski

[57] ABSTRACT

Marker members of radiopaque material in the form of bands each of a different geometric configuration are sutured to the point at which a surgical graft to a blood vessel is made as in a coronary bypass operation. These ring or other shaped radiopaque members provide markers identifying the exact coronary blood vessel that the graft will lead to, each geometrical shape identifying a different coronary vessel bypassed, thus facilitating bypass graft catherization by identifying the entry point of any specific bypass graft.

5 Claims, 8 Drawing Figures

RADIOPAQUE CODED RING MARKERS FOR USE IN IDENTIFYING SURGICAL GRAFTS

This invention relates to surgical procedures and more particularly to such a procedure in which radiopaque markers are utilized to identify the locations of surgical grafts.

Coronary bypass surgery which was first developed in 1967, involves the removal of an expendable vein from the patient's leg, one end of the vein being sewn into the coronary artery beyond the blockage and the other end being sewn into the aorta. In order to identify the location of each bypass, radiopaque markers or tags generally in the form of a clip or washer which is fastened alongside the graft or encircling the graft have been employed. Such prior art devices are described in U.S. Pat. Nos. 4,041,931 issued Aug. 16, 1977 to Elliott, et al. and 4,202,349 issued May 13, 1980 to Jones. This marker usually in the form of a ring is generally placed around the aortic end of the graft prior to completion of the proximal anastomosis. The ring is sutured to the aorta after completion of the proximal anastomosis. Such rings are generally of medical grade stainless steel. Such marking of the graft locations has been found very useful in identifying such locations radiographically in the event that a graft should become blocked or partially blocked so as to require an injection with dye to determine the degree of patency.

Frequently a number of bypass must be performed on the same patient. It has often been found difficult in such situations to specifically identify the origin of a graft as well as the target vessel for each of several grafts with an X-ray so that the cardiologist can properly perform a catheterizing procedure.

The method and device of the present invention overcomes these prior art shortcomings and providing radiopaque markers or tags which positively identify each separate graft on an X-ray. This desired end result is achieved in the present invention by employing band markers of different geometric shapes each of which can be used to identify a different graft site and destination. These markers may be in the form of rings, squares, triangles or any one of these geometric configurations having an opening therein. Typically, the markers are fabricated of a stainless steel band in the desired shape. The squares and triangles are given rounded corners to avoid sharp edges which might be injurious to tissue.

It is therefore an object of this invention to facilitate in chest ray or heart catherization the location of individual bypass grafts where a number of coronary bypasses have been made.

It is a further object of this invention to lessen the hazards involved in catheterizing a post coronary bypass patient.

Other objects of the invention will become apparent as the description proceeds in connection with the accompanying drawings of which:

Figure 1:
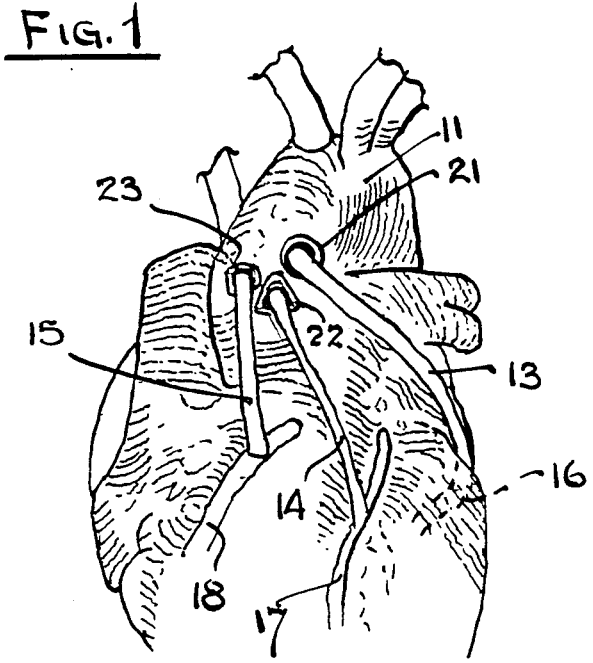
FIG. 1 illustrates the utilization of a device of the invention in identifying individual bypass sites.
Figure 3:
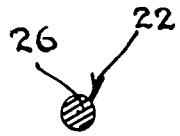
FIG. 3 is a cross sectional view taken along 3—3 in FIG. 2A.

Referring now to FIG. 1, a plurality of bypasses 13, 14 and 15 made by means of vein sections removed from the patient's leg and placed between arteries 16, 17 and 18 and the patient's aorta 11 are shown. These individual grafts are positively identified by means of markers 21 22, and 23, marker 21 being in the shape of a circle marker 22 being in the shape of a triangle and marker 23 being in the shape of a square. These markers may be made of stainless steel bands which are placed around the aortic end of the graft prior to the suturing of the graft to the aorta and then sutured to the aorta.

Referring now to FIGS. 2A-2F, various markers which may be employed are shown. The triangles and squares is to be noted all have rounded corners. The devices are all formed of medical grade stainless steel 26. Each of the markers may be employed to conventionally identify a different grade site and destination or target. For example, 2A-left anterior descending; 2B-circumflex; 2C-right coronary.

Figure 2A:
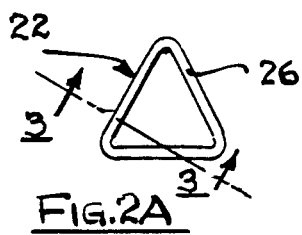
FIGS. 2A-2F illustrate a number of different marker units that may be employed in carrying out the invention.
Figure 2D:
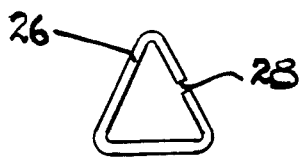
Figure 2B:
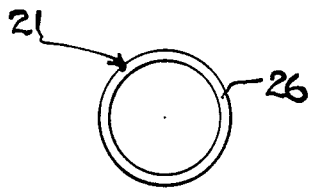
Figure 2E:
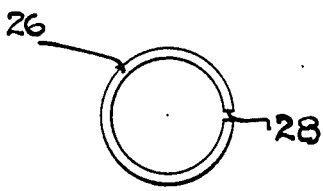
Figure 2C:
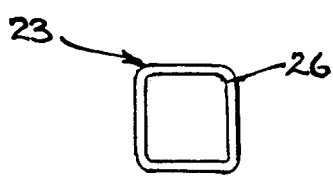
Figure 2F:
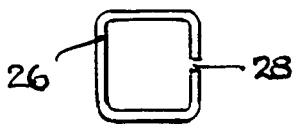

It is to be noted that the markers of FIGS. 2D-2F are triangular, circular or square as are the markers of 2A-2C. However, these markers have a break 28 formed therein which breaks can be identified in the radiograph. These triangular, circular and square markers having breaks therein can be used to identify grafts having as their destination branches of the three main coronary arteries, i.e., the broken triangle of FIG. 2D-branch of left anterior descending; the broken circle of FIG. 2E-branch of circumflex; the broken square of FIG. 2F branch of right coronary.

Thus, by means of the present invention a significant amount of time and exploration can be saved by a cardiologist in catheterizing a post bypass patient. This increases the safety of the procedure for the patient as well as decreasing radiation exposure to both the patient and the personnel involved as well as decreasing the cost of the procedure in view of the reduction in the examination time required.

While the invention has been described and illustrated in detail, it is to be clearly understood that is intended by way of illustration and example only and is not to be taken by way of limitation. The spirit and scope of this invention being limited only by the terms of the following claims.

We claim:

1. A surgical procedure for radiographically identifying each site and destination of a surgical bypass graft comprising the steps of:
   providing a plurality of marker members in the form of bands of a radiopaque material, each of said marker members having a different geometrical configuration, each of such configurations adapted to identify a different preselected graft destination,
   placing each of said differently geometrically configured marker members around a different graft section at the site of the origin of the graft which its configuration is adapted to identify, and
   suturing said markers in place at said graft sites to identify each such destination by virtue of the different geometrical configuration of each of said marker members.

2. The procedure of claim 1 wherein said marker members are fabricated of stainless steel.

3. The procedure of claim 2 wherein certain of said marker members have a break therein to provide additional radiographic identity.

4. The procedure of claim 2 wherein said marker members are respectively in the shape of a circle, a square, and a triangle.

5. The procedure of claim 4 wherein the square and triangle have rounded corners.

* * * * *